United States Patent [19]

Flynn et al.

[11] Patent Number: 5,641,880

[45] Date of Patent: Jun. 24, 1997

[54] PROCESSES FOR PREPARING INTERMEDIATES OF INHIBITORS OF ENKEPHALINASE AND ANGIOTENSIN CONVERTING ENZYME AND INTERMEDIATES THEREOF

[75] Inventors: Gary A. Flynn, Cincinnati; Thomas D. Bannister, Middletown, both of Ohio

[73] Assignee: Hoechst Marion Roussel, Inc., Cincinnati, Ohio

[21] Appl. No.: 535,403

[22] Filed: Oct. 24, 1995

Related U.S. Application Data

[63] Continuation-in-part of Ser. No. 360,915, Dec. 21, 1994, abandoned.

[51] Int. Cl.$^6$ .................................................. C07D 417/04
[52] U.S. Cl. ........................ 540/522; 540/519; 540/521
[58] Field of Search ........................... 540/521, 522, 540/519

[56] References Cited

U.S. PATENT DOCUMENTS

| | | |
|---|---|---|
| 4,824,832 | 4/1989 | Flynn et al. . |
| 4,973,585 | 11/1990 | Flynn et al. . |
| 5,238,932 | 8/1993 | Flynn et al. . |
| 5,430,145 | 7/1995 | Flynn et al. . |
| 5,457,196 | 10/1995 | Warshawsky et al. . |

FOREIGN PATENT DOCUMENTS

| | | |
|---|---|---|
| 0249223 | 12/1987 | European Pat. Off. . |
| 0322914 | 12/1988 | European Pat. Off. . |
| 0481522 | 4/1992 | European Pat. Off. . |
| 0492369 | 7/1992 | European Pat. Off. . |
| 0534363 | 3/1993 | European Pat. Off. . |
| 0599444 | 6/1994 | European Pat. Off. . |
| 0657453 | 6/1995 | European Pat. Off. . |

OTHER PUBLICATIONS

Gary A. Flynn et al, *J. Am. Chem. Soc.*, 1987, vol. 109, p. 7914.
Gary A. Flynn et al, *Peptide Chemistry*, 1987, pp. 631–636.
Flynn, et al., *Tetrahedron Letters*, vol. 31, No. 6, pp. 815–818 (1990).
Todd K. Jones et al., *J. Org. Chem.* 1991, vol. 56, pp. 763–769.
Joseph Foos, et al., *J. Org. Chem.*, vol. 44, No. 14, 1979, pp. 2522 & 2529.
Roy, R.B. et al., *Can. J. Biochem*, vol. 52, 1973, p. 942.

*Primary Examiner*—Patricia I. Morris
*Attorney, Agent, or Firm*—David M. Stemerick

[57] ABSTRACT

The present invention relates to novel processes for preparing intermediates of the formula I

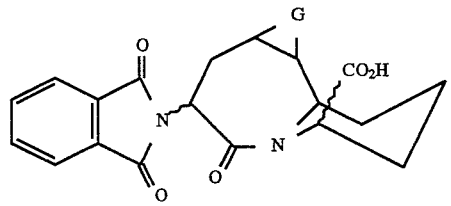

and to novel intermediates thereof which are useful in the preparation of inhibitors of enkephalinase and angiotensin converting enzyme.

3 Claims, No Drawings

PROCESSES FOR PREPARING INTERMEDIATES OF INHIBITORS OF ENKEPHALINASE AND ANGIOTENSIN CONVERTING ENZYME AND INTERMEDIATES THEREOF

BACKGROUND OF THE INVENTION

This is a continuation-in-part of application Ser. No. 08/360,915, filed Dec. 21, 1994, abandoned.

The present invention relates to novel processes for preparing compounds of the formula I,

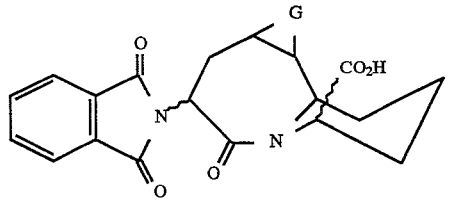

formula I which are useful intermediates for preparing inhibitors of enkephalinase and angiotensin converting enzyme, including [4S-[4α,7α(R*), 12bβ]]-7-[(1-oxo-2(S)-thio-3-phenylpropyl)amino]-1,2,3,4,6,7,8,12b-octahydro-6-oxo-pyrido[2,1-a][2]benzazepine-4-carboxylic acid and [4S-[4α, 7α(R*), 12bβ]]-7-[(1-oxo-2(S)-acetylthio-3-phenylpropyl) amino]-1,2,3,4,6,7,8,12b-octahydro-6-oxo-pyrido[2,1-a][2] benzazepine-4-carboxylic acid and pharmaceutically acceptable salts thereof (European Patent Application No. 0 481 522 A1, published 22 Apr. 1992, 209th ACS National Meeting, Division of Medicinal Chemistry, Abst. No. 161 (1995), and European Patent Application No. 657 453 A1, published 14 Jun. 1995) and to novel intermediates thereof.

SUMMARY OF THE INVENTION

The present invention provides a novel process for preparing a compound of formula I

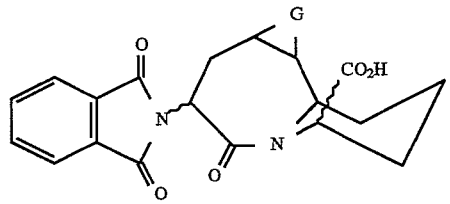

formula I wherein

G completes an aromatic ring selected from the group consisting of

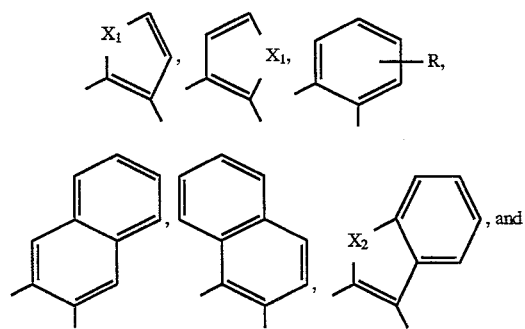

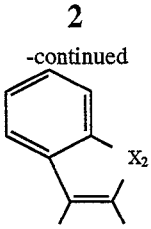

wherein $X_1$ is selected from the group consisting of S and NH;

$X_2$ is selected from the group consisting of S, O, and NH; and

R is selected from the group consisting of hydrogen, hydroxy, phenyl, and $C_1$–$C_4$ alkoxy;

comprising:

(a) reacting a phthalimido aryl amino acid amide of the formula

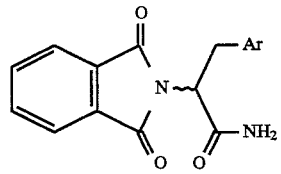

wherein

Ar is a radical selected from the group consisting of

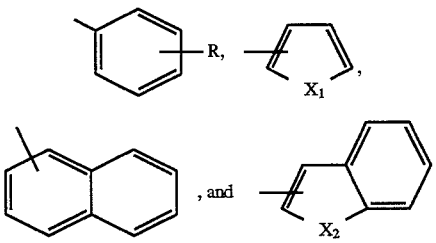

wherein $X_1$ is selected from the group consisting of S and NH;

$X_2$ is selected from the group consisting of S, O, and NH; and

R is selected from the group consisting of hydrogen, hydroxy, phenyl and $C_1$–$C_4$ alkoxy;

with glutaric dialdehyde to give a 1,4-dihydropyridine derivative of the formula

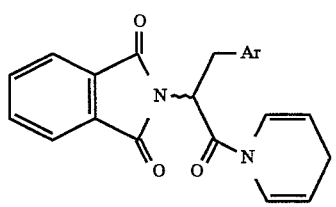

wherein Ar is as defined above;

(b) reacting the 1,4-dihydropyridine derivative with an appropriate cyclizing acid to give a 1,2,6,7,8,12b hexahydro-6-oxopyrido[2,1-a][2]azepine of the formula

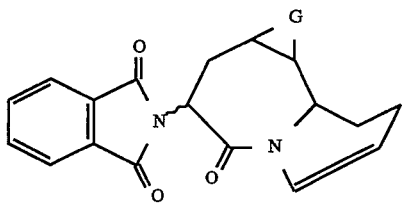

wherein G is as defined above;

(c) reacting the 1,2,6,7,8,12b hexahydro-6-oxopyrido[2,1-a][2]azepine with carbon monoxide in the presence of a suitable acid followed by hydration.

In addition, the present invention provides a novel process for preparing a compound of formula I

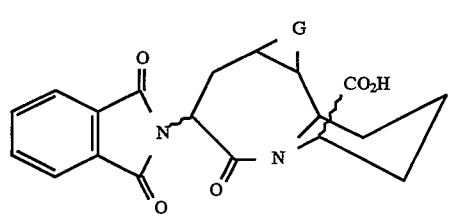

formula I wherein

G completes an aromatic ring selected from the group consisting of

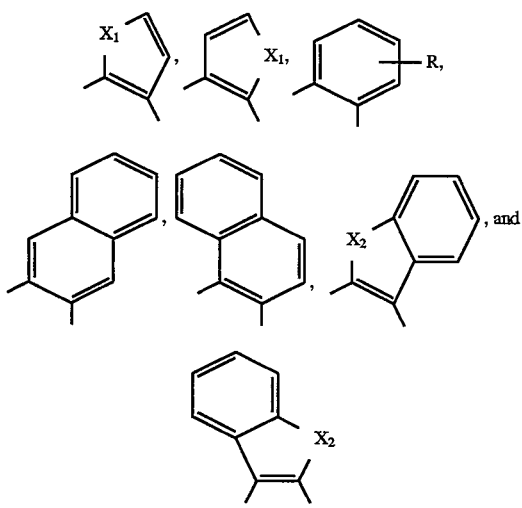

wherein $X_1$ is selected from the group consisting of S and NH;

$X_2$ is selected from the group consisting of S, O, and NH; and

R is selected from the group consisting of hydrogen, hydroxy, phenyl, and $C_1$-$C_4$ alkoxy;

comprising:

(a) reacting a phthalimido aryl amino acid derivative of the formula

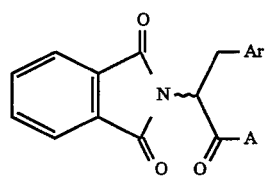

wherein

A is selected from the group consisting of —OH, —Cl, —Br, anhydride, mixed anhydride, and activated ester;

Ar is a radical selected from the group consisting of

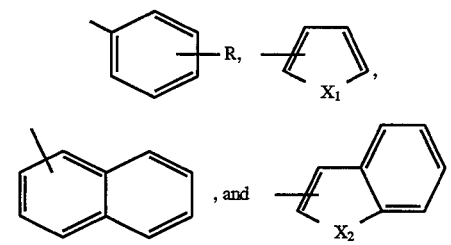

wherein $X_1$ is selected from the group consisting of S and NH;

$X_2$ is selected from the group consisting of S, O, and NH; and

R is selected from the group consisting of hydrogen, hydroxy phenyl and $C_1$-$C_4$ alkoxy;

with 2-cyano-1,2,3,4-tetrahydro-pyridine to give a 2-cyano-1,2,3,4-tetrahydro-pyridine derivative of the formula

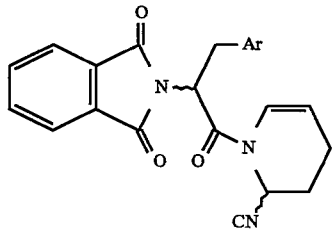

wherein Ar is as defined above;

(b) reacting the 2-cyano-1,2,3,4-tetrahydro-pyridine derivative with an appropriate cyclizing acid to give a -cyano-1,2,3,4,6,7,8,12b-octahydro-6-oxopyrido[2,1-a][2]benzazepine of the formula

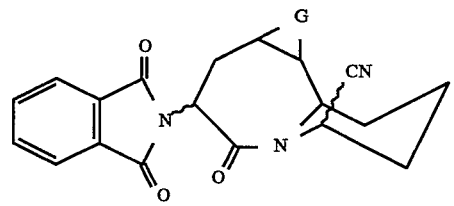

wherein G is as defined above;

(c) hydrolyzing the 4-cyano-1,2,3,4,6,7,8,12b-octahydro-6-oxopyrido[2,1-a][2]benzazepine.

The present invention provides a novel compound of the formula:

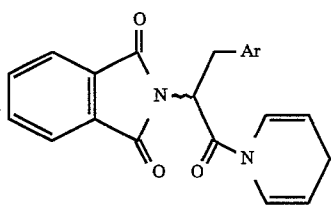

wherein

Ar is a radical selected from the group consisting of

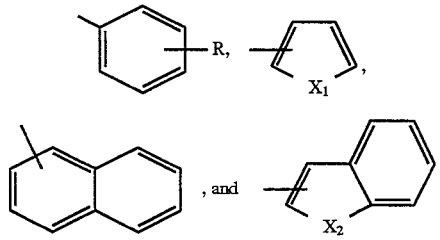

wherein

X₁ is selected from the group consisting of S and NH;
X₂ is selected from the group consisting of S, O, and NH; and
R is selected from the group consisting of hydrogen, hydroxy, phenyl, and C₁–C₄ alkoxy.

In addition, the present invention provides a novel compound of the formula:

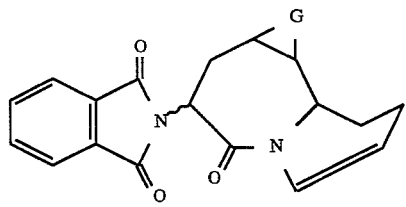

wherein

G completes an aromatic ring selected from the group consisting of

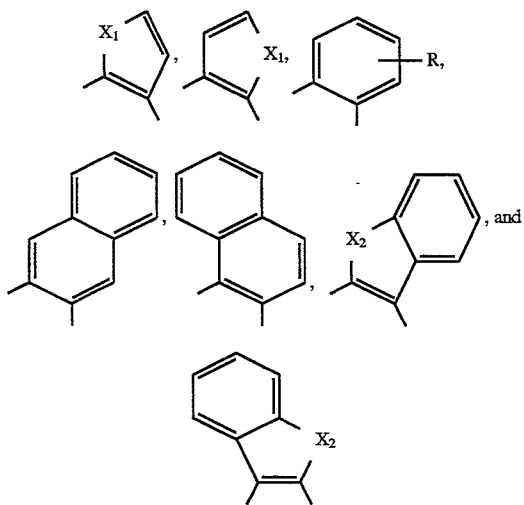

wherein

X₁ is selected from the group consisting of S and NH;

X₂ is selected from the group consisting of S, O, and NH; and

R is selected from the group consisting of hydrogen, hydroxy, phenyl, and C₁–C₄ alkoxy.

In addition, the present invention provides a novel compound of the formula:

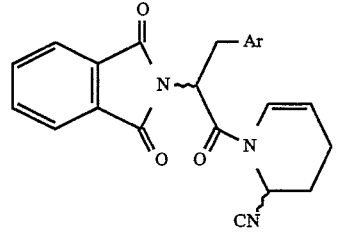

wherein

Ar is a radical selected from the group consisting of

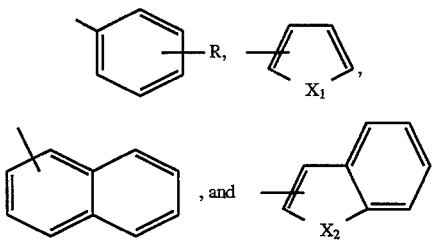

wherein

X₁ is selected from the group consisting of S and NH;

X₂ is selected from the group consisting of S, O, and NH; and

R is selected from the group consisting of hydrogen, hydroxy, phenyl, and C₁–C₄ alkoxy.

In addition, the present invention provides a novel compound of the formula:

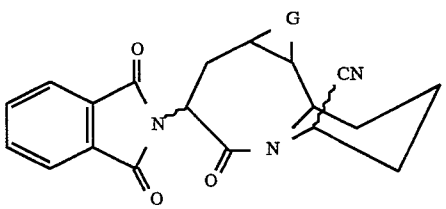

wherein

G completes an aromatic ring selected from the group consisting of

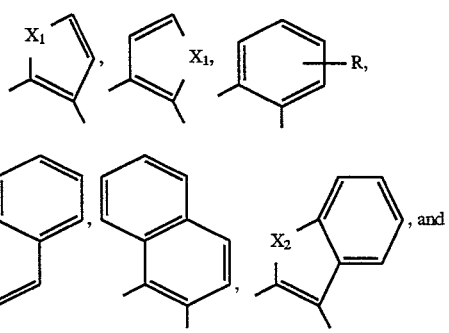

-continued

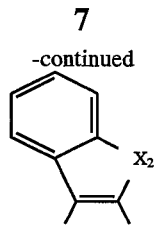

wherein $X_1$ is selected from the group consisting of S and NH;

$X_2$ is selected from the group consisting of S, O, and NH; and

R is selected from the group consisting of hydrogen, hydroxy, phenyl, and $C_1$–$C_4$ alkoxy.

DETAILED DESCRIPTION OF THE INVENTION

As used in this application:

a) the designation

" ▶ "

refers to a bond that protrudes forward out of the plane of the page;

b) the designation

" ⅲ "

refers to a bond that protrudes backward out of the plane of the page;

c) the designation

" ∼ "

refers to a bond for which the stereochemistry is not designated;

d) the term "$C_1$–$C_4$ alkoxy" refer to a straight or branched alkoxy group containing from 1 to 4 carbon atoms, such as methoxy, ethoxy, n-propoxy, isopropoxy, n-butoxy, isobutoxy, t-butoxy, etc;

e) the term "phenyl" refers to a radial of the formula

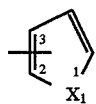

f) the designation

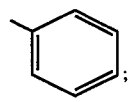

refers to a thienyl or pyrrolyl and it is understood that the radical may be attached at either the 2-position or the 3-position;

g) the designation

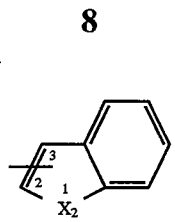

refers to an indolyl, benzthienyl, or benzfuryl and it is understood that the radical may attached at either the 2-position or the 3-position;

h) the designation

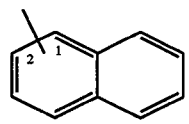

refers to a naphthyl it is understood that the radical can be attached at either the 1-position or the 2-position;

i) it is understood that when G completes an aromatic ring

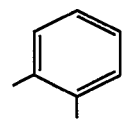

that the compound of formula I is of the formula

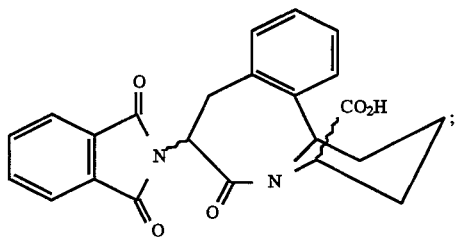

j) it is understood that when G completes an aromatic ring

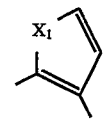

that the compound of formula I is of the formula

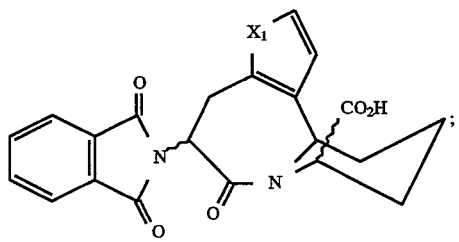

k) it is understood that when G completes an aromatic ring

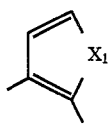

that the compound of formula I is of the formula

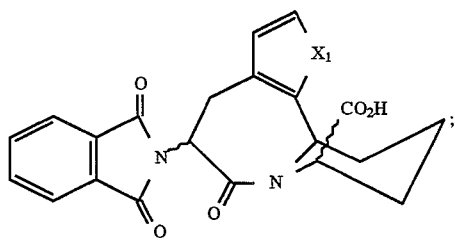

l) it is understood that when G completes an aromatic ring

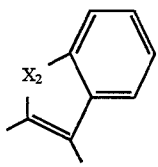

that the compound of formula I is of the formula

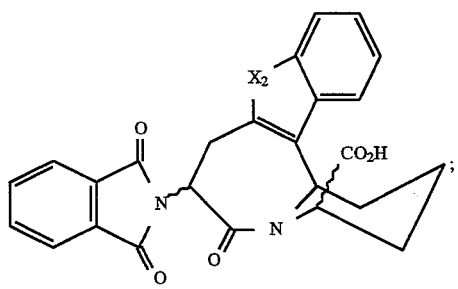

m) it is understood that when G completes an aromatic ring

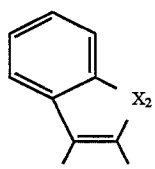

that the compound of formula I is of the formula

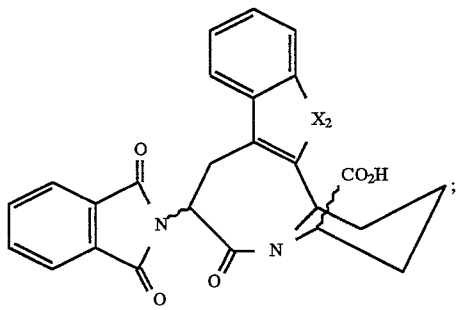

n) it is understood that when G completes an aromatic ring

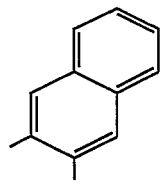

that the compound of formula I is of the formula

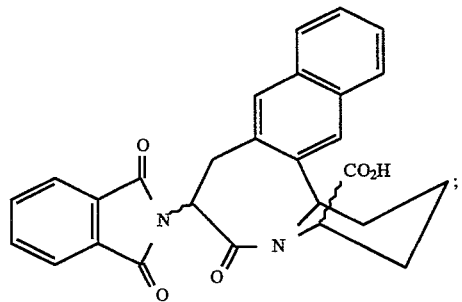

o) it is understood that when G completes an aromatic ring

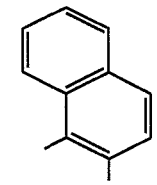

that the compound of formula I is of the formula

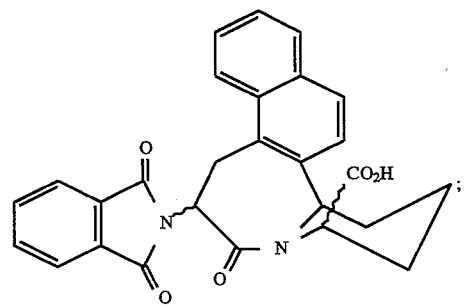

p) the term "pharmaceutically acceptable salts" refers to either acid addition salts or to base addition salts.

The expression "pharmaceutically acceptable acid addition salts" is intended to apply to any non-toxic organic or inorganic acid addition salt of inhibitors of enkephalinase and angiotensin converting enzyme, including [4S-[4α, 7β(R*), 12bβ]]-7-[(1-oxo-2(S)-thio-3-phenylpropyl)amino]-1,2,3,4,6,7,8,12b-octahydro-6-oxo-pyrido[2,1-a][2]benzazepine-4-carboxylic acid or [4S-[4α, 7β(R*), 12bβ]]-7-[(1-oxo-2(S)-acetylthio-3-phenylpropyl)amino]-1,2,3,4,6,7,8,12b-octahydro-6-oxo-pyrido[2,1-a][2]benzazepine-4-carboxylic acid or any intermediates thereof. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, and sulfonic acids such as p-toluenesulfonic acid, methane sulfonic acid and 2-hydroxyethane sulfonic acid. Such salts can exist in either a hydrated or substantially anhydrous form.

The expression "pharmaceutically acceptable basic addition salts" is intended to apply to any non-toxic organic or inorganic basic addition salts of inhibitors of enkephalinase and angiotensin converting enzyme, including [4S-[4α, 7β(R*), 12bβ]]-7-[(1-oxo-2(S)-thio-3-phenylpropyl)amino]-1,2,3,4,6,7,8,12b-octahydro-6-oxo-pyrido[2,1-a][2]benzazepine-4-carboxylic acid or [4S-[4α, 7β(R*), 12bβ]]-7-[(1-oxo-2(S)-acetylthio-3-phenylpropyl)amino]-1,2,3,4,6,7,8,12b-octahydro-6-oxo-pyrido[2,1-a][2]benzazepine-4-carboxylic acid or any intermediates thereof. Illustrative bases which form suitable salts include alkali metal or alkaline-earth metal hydroxides such as sodium, potassium, calcium, magnesium, or barium hydroxides; ammonia, and aliphatic, cyclic, or aromatic organic amines such as methylamine, dimethylamine, trimethylamine, triethylamine, diethylamine, isopropyldiethylamine, pyridine and picoline.

As is appreciated by one of ordinary skill in the art, the methodology disclosed herein can be used to prepare all isomers at the 4-position and 7-postition of instant intermediates, including 7-[(1,3-dihydro-1,3-dioxo-2H-isoindol-2-yl)]-1,2,3,4,6,7,8,12b-octahydro-6-oxopyrido[2,1-a][2]benzazepine-4-carboxylic acid and thereby the isomers of the inhibitors of enkephalinase and angiotensin converting enzyme produced therefrom. The stereochemistry at the 7-position of the intermediates is determined by the stereochemistry of the phthalimido aryl amino acid amide or the activated phthalimido aryl amino acid derivative selected. The specific 4-position stereoisomers can be resolved and recovered by techniques known in the art, such as chromatography on silica gel or on a chiral stationary phase, or fractional recrystallization of the 4-position carboxylic acids or derivatives thereof as described herein; in European Patent Application No. 0 481 522 A1, published 22 April 1992; Stereochemistry of Organic Compounds, E. L. Eliel and S. H. Wilen, Wiley (1994); and in Enantiomers, Racemates, and Resolutions, J. Jacques, A. Collet, and S. H. Wilen, Wiley (1981).

A general synthetic procedure is set forth in Scheme A. In Scheme A, all substituents unless otherwise indicated, are as previously defined. Starting materials, reagents, techniques and procedures used in Scheme A are well known and appreciated by one of ordinary skill in the art.

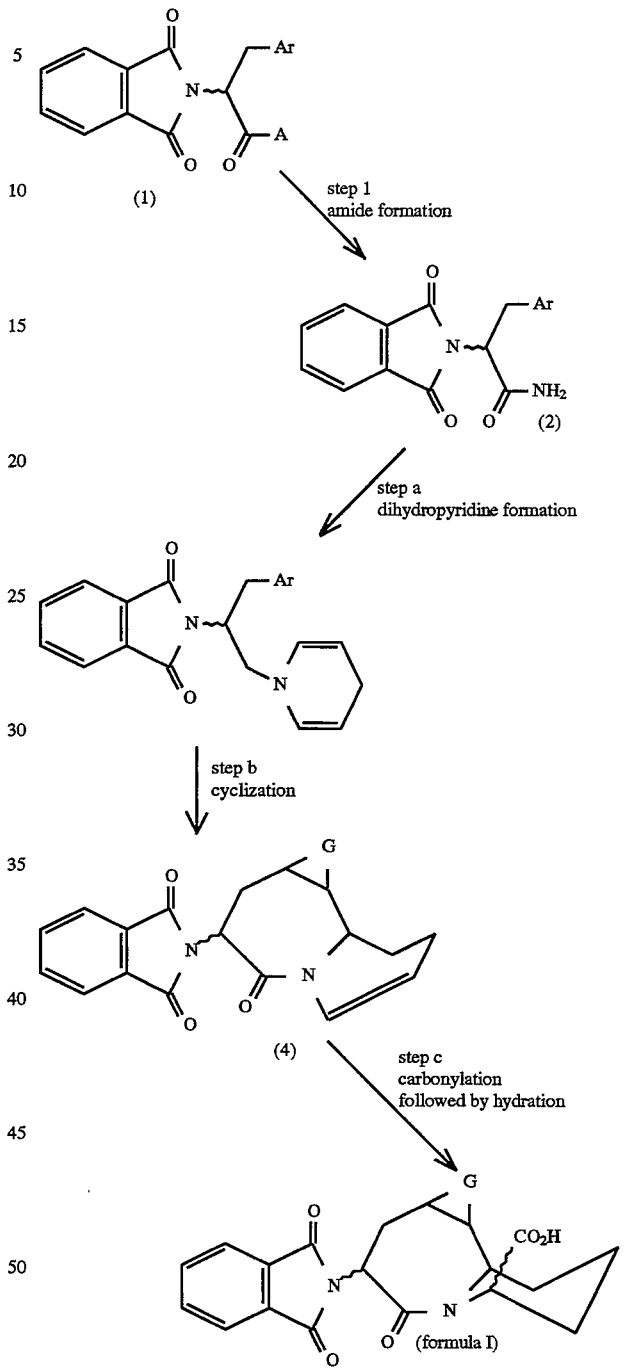

In Scheme A, step 1, an appropriate phthalimido aryl amino acid derivative of structure (1) is contacted with ammonia to give a phthalimido aryl amino acid amide of structure (2) as is well known in the art.

In Scheme A, step a, an appropriate phthalimido aryl amino acid amide of structure (2) is contacted with glutaric dialdehyde to give a 1,4-dihydro-pyridine derivative of structure (3).

An appropriate phthalimido aryl amino acid amide derivative of structure (2) are readily available or are readily derived from aromatic amino acids which are well known in the art. Examples of aromatic amino acids which are useful in this instant process include: phenylalanine, tryptophan, tyrosine and its ether derivatives, thien-2-ylalanine, 3-thienylalanine, fur-2-ylalanine, fur-3-ylalanine, benzthien-2-ylalanine, indol-2-ylalanine, etc. *The Peptides*, vol. 5, E. Gross and J. Meienhoffer ed. (Academic Press, 1983). In addition, aromatic amino acids can be obtained by methods known in the art or analogously known in the art, such as D. A. Evans, et al. *J. Am. Chem. Soc.*, 112, 4011–4030 (1990); S. Ikegami et al. *Tetrahedron* 44, 5333–5342 (1988); W. Oppolzer et al. *Tet. Lets.* 30, 6009–6010 (1989); *Synthesis of Optically Active α-Amino-Acids*, R. M. Williams (Pergamon Press, Oxford 1989); M. J. O'Donnell ed.: *α-Amino-Acid Synthesis, Tetrahedron* Symposia in print, No. 33, *Tetrahedron* 44, No. 17 (1988); U. Schöllkopf, *Pure Appl. Chem.* 55, 1799 (1983); U. Hengartner et al. *J. Org. Chem.*, 44, 3748–3752 (1979); M. J. O'Donnell et al. *Tet. Lets.*, 2641–2644 (1978); M. J. O'Donnell et al. *Tet. Lets.* 23, 4255–4258 (1982); M. J. O'Donnell et al. *J. Am. Chem. Soc.* 110, 8520–8525 (1988).

An appropriate phthalimido aryl amino acid amide of structure (2) is one in which the stereochemistry is as desired in the final product and Ar is as required to give G as desired in the final product. It is understood that glutaric dialdehyde can be generated in the reaction mixture from a suitable glutaric dialdehyde equivalent. Suitable glutaric dialdehyde equivalents include acetals of glutaric dialdehyde, hydrated forms of glutaric dialdehyde, and the like.

For example, an appropriate phthalimido aryl amino acid amide of structure (2) is contacted with from about 0.9 to 1.2 molar equivalents of glutaric dialdehyde. The reaction is carried out in a suitable solvent, such as dichloromethane. The reaction is carried out under acidic catalysis. Suitable catalysts are well known in the art and include p-toluenesulfonic acid. The reaction is carried out at from ambient temperature to the refluxing temperature of the solvent. The reaction is carried out with the removal of water by methods well known in the art, such as by azeotrope, by passing the refluxate over or through a drying agent, such as phosphorous pentoxide or by carrying out the reaction in the presence of a suitable non-reactive drying agent, such as 3Å molecular sieves, 4Å molecular sieves, $MgSO_4$, and the like. Generally, the reaction requires from 2 hours to 4 days. The product can be isolated and purified by techniques well known in the art, such as extraction, evaporation, chromatography, and recrystallization.

In Scheme A, step b, an appropriate 1,4-dihydro-pyridine derivative of structure (3) is contacted with an appropriate cyclizing acid to give a 1,2,6,7,8,12b hexahydro-6-oxopyrido[2,1-a][2]azepine of structure (4).

For example, an appropriate 1,4-dihydro-pyridine derivative of structure (3) is contacted with an appropriate cyclizing acid. An appropriate cyclizing acid is one which allows for the formation of product without leading to significant degradation of either the starting material or the product. Examples appropriate cyclizing acids include, sulfuric acid, trifluoromethanesulfonic acid, sulfuric acid/trifluoroacetic anhydride mixtures, and trifluoromethanesulfonic acid/ trifluoroacetic anhydride mixtures. The reaction is carried out neat in the appropriate cyclizing acid selected or in a suitable aprotic solvent, such as dichloromethane. The reaction is carried out at temperatures of from 10° C.–40° C. Generally the reaction requires from 1 to 8 hours. The product can be isolated and purified by techniques well known in the art, such as extraction, evaporation, chromatography, and recrystallization.

In Scheme A, step c, an appropriate 1,2,6,7,8,12b hexahydro-6-oxopyrido[2,1-a][2]azepine of structure (4) is contacted with carbon monoxide in the presence of a suitable acid followed by hydration to give a compound of the formula I.

For example, an appropriate 1,2,6,7,8,12b hexahydro-6-oxopyrido[2,1-a][2]azepine of structure (4) is contacted with an excess of carbon monoxide in the presence of a suitable acid, such as sulfuric acid, followed by hydration. The reaction is carried out using the suitable acid selected as solvent. The reaction may be carried out in a suitable pressure vessel to prevent the escape of carbon monoxide. Carbon monoxide may be introduced as a gas or may be generated in the reaction vessel by methods well known in the art, such as the decomposition of formic acid. The reaction is carried out at temperatures of from 0° to 100° C. The reaction may be carried out at pressures of from atmospheric pressure to 900 psi. When the reaction is carried out at a pressure which is greater than atmospheric the use of a suitable pressure vessel, such as sealed or sealable tubes, a pressure reactor or an autoclave, is required. Generally the reaction requires from 1 to 48 hours. The addition of carbon monoxide is followed by hydration which is accomplished by the addition of water. The product can be isolated and purified by techniques well known in the art, such as extraction, evaporation, chromatography, and recrystallization.

A general synthetic procedure is set forth in Scheme B. In Scheme B, all substituents unless otherwise indicated, are as previously defined. Starting materials, reagents, techniques, and procedures used in Scheme B are well known and appreciated by one of ordinary skill in the art.

SCHEME B

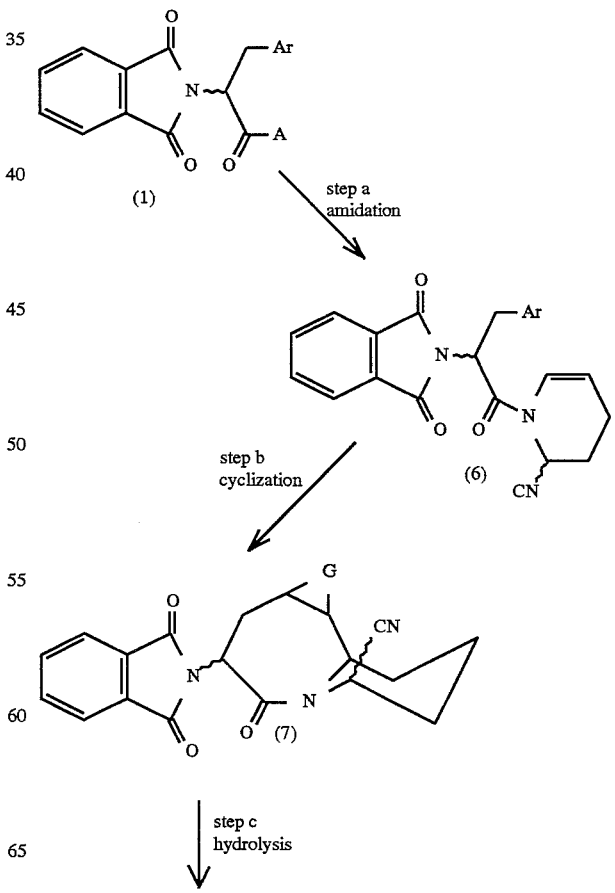

-continued
SCHEME B

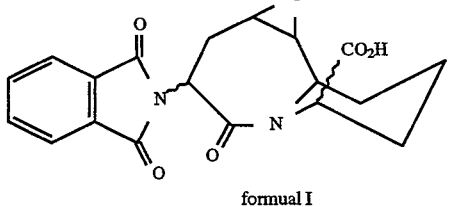

formula I

In Scheme B, step a, an appropriate phthalimido aryl amino acid derivative of structure (1) is contacted with 2-cyano-1,2,3,4-tetrahydro-pyridine to give a 2-cyano-1,2,3,4-tetrahydro-pyridine derivative of structure (6).

An appropriate phthalimido aryl amino acid derivative are readily available or are readily derived from aromatic amino acids which are well known in the art as described in Scheme A, step a.

An appropriate phthalimido aryl amino acid derivative is one in which the stereochemistry is as desired in the final product, Ar is as required to give G as desired in the final product, and the group A is an activating group which can be displaced by 2-cyano-1,2,3,4-tetrahydro-pyridine in an amidation reaction. An amidation reaction may proceed through an acid, A is —OH; or an acid halide, such as an acid chloride, A is —Cl; or acid bromide, A is —Br; or an activated intermediate; such as an anhydride; or a mixed anhydride of substituted phosphoric acid, such as dialkylphosphoric acid, diphenylphosphoric acid, halophosphoric acid; of aliphatic carboxylic acid, such as formic acid, acetic acid, propionic acid, butyric acid, isobutyric acid, pivalic acid, 2-ethylbutyric acid, trichloroacetic acid, trifluoroacetic acid, and the like; of aromatic carboxylic acids, such as benzoic acid and the like; of an activated ester, such as phenol ester, p-nitrophenol ester, 2,4-dinitrophenol ester, pentafluorophenol ester, pentachlorophenol ester, N-hydroxysuccinimide ester, N-hydroxyphthalimide ester, 1-hydroxy-1H-benztriazole ester, and the like; activated amide, such as imidazole, dimethylpyrazole, triazole, or tetrazole; or an intermediate formed in the presence of coupling agents, such as dicyclohexylcarbodiimide or 1-(3-dimethylaminopropyl)-3-ethylcarbodiimide. Acid halides and activated intermediates may be prepared and used without isolation. Alternately, acid halides and activated intermediates may be prepared and isolated but not purified before use. The use and formation of acid halides and activated intermediates is well known and appreciated in the art.

For example, an appropriate phthalimido aryl amino acid derivative of structure (1) in which A is —Cl is contacted with a molar excess of 2-cyano-1,2,3,4-tetrahydro-pyridine which can be generated in situ by reacting 2,6-dicyano-piperidine with a suitable base such as potassium t-butoxide. The reaction is carried out in a suitable solvent, such as, tetrahydrofuran. The amide formation reaction is carried out using a suitable base, such as N-methylmorpholine. The reaction is carried out at temperatures of from −50° C. to 40° C. and generally requires from 1 hour to 5 hours. The product can be isolated and purified by techniques well known in the art, such as filtration, evaporation, extraction, chromatography, and recrystallization.

In Scheme B, step b, an appropriate 2-cyano-1,2,3,4-tetrahydro-pyridine derivative of structure (6) is contacted with an appropriate cyclizing acid to give a 4-cyano-1,2,3,4,6,7,8,12b-octahydro-6-oxopyrido[2,1-a][2]benzazepine of structure (7).

An appropriate cyclizing acid is one which allows for the formation of product without leading to significant degradation of either the starting material or the product. Examples of appropriate cyclizing acids include, sulfuric acid, trifluoromethanesulfonic acid, sulfuric acid/ trifluoroacetic anhydride mixtures, and trifluoromethanesulfonic acid/trifluoroacetic anhydride mixtures.

For example, an appropriate 2-cyano-1,2,3,4-tetrahydro-pyridine derivative of structure (6) is contacted with an appropriate cyclizing acid. The reaction is carried out neat in the appropriate cyclizing acid selected or in a suitable aprotic solvent, such as dichloromethane. The reaction is carried out at temperatures of from 10° C.–40° C. and generally requires from 1 to 18 hours. It is preferred that the product of this step, obtained in solution, be used without isolation, however, the product can be isolated and purified by techniques well known in the art, such as extraction, evaporation, chromatography, and recrystallization.

In Scheme B, step c, an appropriate 4-cyano-1,2,3,4,6,7,8,12b-octahydro-6-oxopyrido[2,1-a][2]benzazepine of structure (7) is hydrolyzed to give a compound of the formula I.

For example, an appropriate 4-cyano-1,2,3,4,6,7,8,12b-octahydro-6-oxopyrido[2,1-a][2]benzazepine of structure (7) is contacted with water. The reaction is carried out in the presence of a suitable acid catalyst. A suitable acid catalyst is one which allows for the hydrolysis of a cyano group, under the reaction conditions, to a carboxylic acid without removing the phthalimide group or hydrolyzing the cyclic amide bond. Suitable acid catalysts are well known in the art and include, sulfuric acid, trifluoromethanesulfonic acid, trifluoromethanesulfonic acid/trifluoroacetic acid mixtures and sulfuric acid/trifluoroacetic anhydride mixtures. When the product of the previous step is used without isolation the appropriate cyclizing acid selected may be used as the suitable acid catalyst for the hydrolysis. The reaction is carried out at temperatures of from about 10° C. to about 40° C. Generally the reaction requires from 10 minutes to 2 hours. The product can be isolated and purified by techniques well known in the art, such as extraction, evaporation, chromatography, and recrystallization.

The following examples present typical syntheses as described in Schemes A and B. These examples and preparations are understood to be illustrative only and are not intended to limit the scope of the invention in any way. As used in the following examples and preparations, the following terms have the meanings indicated: "mg" refers to milligrams, "g" refers to grams, "kg" refers to kilograms, "mmol" refers to millimoles, "mol" refers to moles, "µL" refers to microliters, "mL" refers to milliliters, "L" refers to liters, "°C." refers to degrees Celsius, "mp" refers to melting point, "dec" refers to decomposition, "$[\alpha]^2_D{}^{0}$" refer to specific rotation of the D line of sodium at 20° C. obtained in a 1 decimeter cell, "c" refers to concentration in g/100 mL, "M" refers to molar, "L" refers to liter, "2-PrOH" refers to isopropanol, "MeOH" refers to methanol, "$R_f$" refers to retention factor, "TLC" refers to thin layer chromatography, "psi" refers to pounds per square inch.

PREPARATION 1

Synthesis of N-Phthaloyl-(S)-phenylalanine, acid chloride

Combine phthalic anhydride (1.82 kg, 12.3 mole), (S)-phenylalanine (1.84 kg, 11.1 moles) and anhydrous dimethylformamide (2.26 L). Stir at 115°–120° C. for 2 hours under a nitrogen atmosphere. Pour into rapidly stirred water (32.6

L) and cool overnight at 0° C. Filter, wash with cold water (2×2 L), and air dry. Dissolve in a mixture of 9A ethanol (8.05 L) and water (8.05 L) and heat at reflux temperature. Gravity filter, cool to ambient temperature and refrigerate overnight at about 0° C. Filter the crystallized product, wash with cold 50:50 9A ethanol/water (2×2 L) and air dry to yield 2.96 kg (90.3%) of N-phthaloyl-(S)-phenylalanine; mp 177°–179° C.

Combine N-phthaloyl-(S)-phenylalanine (50.2 g, 0.17 mol), methylene chloride (660 mL) and dimethylformamide (0.5 mL) under a nitrogen atmosphere. Add oxalyl chloride (17.7 mL, 0.2 mol) over about 5 minutes. Stir at ambient temperature for 3 hours and evaporate the solvent in vacuo to give the title compound.

PREPARATION 2

Synthesis of Phthalimido-( S)-phenylalanine amide

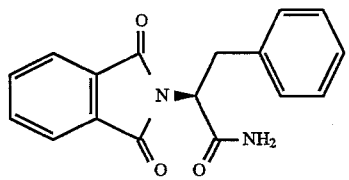

Combine N-phthaloyl-(S)-phenylalanine, acid chloride (100 mmol) and hexane (100 mL). Add a concentrated aqueous ammonia solution (30 mL) and stir rapidly. After 10 minutes, filter, rinse with diethyl ether and water, and dry in vacuo to give the title compound as a solid.

PREPARATION 3

Synthesis of 2,6-Dicyano-piperidine

Combine sodium cyanide (12.25 g, 250 mmol) and water (40 mL). Add ammonium chloride (20 g, 374 mmol) and 30% aqueous ammonia solution (35 mL, 620 mmol). Cool in an ice-bath. Add glutaric dialdehyde (25 mL, 50% in water, mmol). After 7 hours in an ice bath, cool in a bath using a ice/methanol mixture to form a solid. Collect the solid by filtration, rinse with water, and dry to give the title compound.

EXAMPLE 1

(S)-N-[2-(1,3-Dihydro-1,3-dioxo-2H-isoindol-2-yl)-1-oxo-3-phenylpropyl]-1,4-dihydro-pyridine

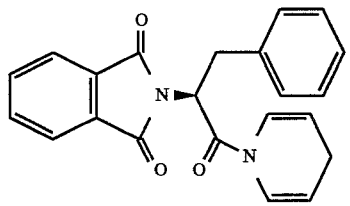

Combine phthalimido-(S)-phenylalanine amide (3.0 g, 10 mmol) and a solution of glutaric dialdehyde (2.0 g, 50% by weight in water) in dichloromethane (200 mL). Heat to reflux with azeotropic removal of water from the refluxate. Add p-toluenesulfonic acid (60 mg). Continue heating at reflux. Pass the refluxate through oven dried 4Å molecular sieves. After 4 days, cool the reaction mixture to ambient temperature. Extract with 5% sodium bicarbonate solution. Extract the 5% sodium bicarbonate solution with dichloromethane. Combine the organic layers and dry over Na$_2$SO$_4$, filter, and evaporate in vacuo to give a residue. Chromatograph the residue on silica gel eluting with 5% tetrahydrofuran/dichloromethane to give the title compound.

EXAMPLE 1.1

(S)-N-[2-(1,3-Dihydro-1,3-dioxo-2H-isoindol-2-yl)-1-oxo-3-phenylpropyl]-1,4-dihydro-pyridine Combine phthalimido-(S)-phenylalanine amide (6.0 g, 20 mmol) and a solution of glutaric dialdehyde (4.0 mL, 50% by weight in water) in dichloromethane (300 mL). Heat to reflux with azeotropic removal of water from the refluxate using a Dean-Stark trap. Add p-toluenesulfonic acid (600 mg). Continue heating at reflux with azeotropic removal of water. Replace the Dean-Stark trap with a Soxhlet extractor charged with phosphorous pentoxide and continue heating at reflux. After 24 hours, cool the reaction mixture to ambient temperature. Add basic alumina to form a slurry. Filter the slurry through a plug of silica gel and elute with dichloromethane. Evaporate the filtrate in vacuo to give the title compound.

EXAMPLE 2

(S)-7-[(1,3-Dihydro-1,3-dioxo-2H-isoindol-2-V1)]-1,2,6,7,8,12b-hexahydro-6-oxopyrido[2,1-a][2] benzazepine

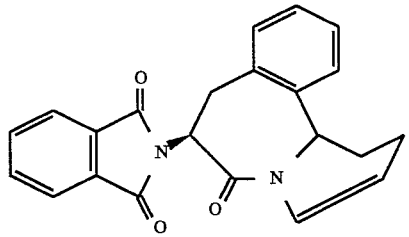

Add a solution of (S)-N-[2-(1,3-dihydro-1,3-dioxo-2H-isoindol-2-yl)-1-oxo-3-phenylpropyl]-1,4-dihydro-pyridine (1.1 g, 3.1 mmol) in dichloromethane (2 mL) to trifluoromethanesulfonic acid (1.2 mL). After 2.5 hours, add trifluoromethanesulfonic acid (1.2 mL). After 4 hours, partition the reaction mixture between ethyl acetate and 5% sodium bicarbonate solution. Dry the organic layer over Na$_2$SO$_4$, filter, and evaporate in vacuo to give a residue. Chromatograph the residue on silica gel eluting sequentially with 10% ethyl acetate/hexane and then 25% ethyl acetate/hexane to give the title compound.

EXAMPLE 2.1

(S)-7-[(1,3-Dihydro-1,3-dioxo-2H-isoindol-2-yl)]-1,2,6,7,8,12b-hexahydro-6-oxopyrido[2,1-a][2] benzazepine Combine sulfuric acid (3.0 mL, 96%) and trifluoroacetic anhydride (300 mL). Add (S)-N-[2-(1,3-dihydro-1,3-dioxo-2H-isoindol-2-yl)-1-oxo-3-phenylpropyl]-1,4-dihydro-pyridine (1.0 mmol). After 30 minutes, pour the reaction mixture into a mixture of saturated aqueous sodium bicarbonate and ice. Extract with ethyl acetate and then with methylene chloride. Combine the organic layers and filter through a plug of silica gel. Rinse the silica gel with dichloromethane. Evaporate the filtrate in vacuo to give a residue. Chromatograph the residue on silica gel eluting sequentially with 10% ethyl acetate/hexane and then 25% ethyl acetate/hexane to give the title compound.

EXAMPLE 3

(S)-7-[(1,3-Dihydro-1,3-dioxo-2H-isoindol-2-yl)]-1,2,3,4,6,7,8f12b-octahydro-6-oxopyrido[2,1-a][2]benzazepine-4-carboxylic acid

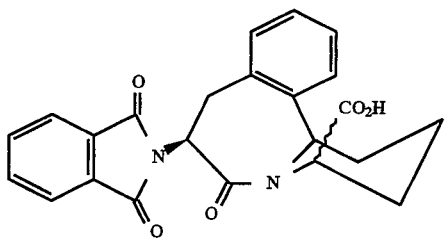

Combine (S)-7-[(1,3-dihydro-1,3-dioxo-2H-isoindol-2-yl)]-1,2,6,7,8,12b-hexahydro-6-oxopyrido[2,1-a][2]benzazepine (32 mg, 0.09 mmol) and sulfuric acid (1.0 mL, 95–98%) in a pressure vessel. Add 96% formic acid (200 μL) and quickly seal the vessel. After 18 hours, add water (10 mL). Extract the reaction mixture with ethyl acetate. Extract the organic layer with saturated aqueous potassium carbonate solution (5×10 mL). Combine the aqueous layers and carefully acidify with aqueous 12M hydrochloric acid solution. Extract with chloroform (5×15 mL). Combine the organic layers, dry over MgSO$_4$, filter, and evaporate in vacuo to give a residue. Chromatograph the residue on silica gel eluting with 2/1 ethyl acetate/hexane containing 0.5% acetic acid to give the title compound. $R_f$=0.14 (silica gel, 2/1 ethyl acetate/hexane containing 0.5% acetic acid).

EXAMPLE 3.1

(S)-7-[(1,3-Dihydro-1,3-dioxo-2H-isoindol-2-yl)]-1,2,3,4,6,7,8,12b-octahydro-6-oxopyrido[2,1-a][2]benzazepine-4-carboxylic acid Combine (S)-7-[(1,3-dihydro-1,3-dioxo-2H-isoindol-2-yl)]-1,2,6,7,8,12b-hexahydro-6-oxopyrido[2,1-a][2]benzazepine (67 mg, 0.19 mmol) and sulfuric acid (2.0 mL, 95–98%) in a pressure vessel. Add 96% formic acid (400 μL) and quickly seal the vessel. After 18 hours, open the vessel cautiously and add ice-cold water (5 mL). Extract the reaction mixture repeatedly with chloroform. Combine the organic layers, dry over MgSO$_4$, filter, and evaporate in vacuo to give a residue. Chromatograph the residue on silica gel eluting with 2/1/0.01 ethyl acetate/hexane/acetic acid to give the title compound.

EXAMPLE 3.2

(S)-7-[(1,3-Dihydro-1,3-dioxo-2H-isoindol-2-yl)]-1,2,3,4,6,7,8,12b-octahydro-6-oxopyrido[2,1-a][2]benzazepine-4-carboxylic acid Combine (S)-7-[(1,3-dihydro-1,3-dioxo-2H-isoindol-2-yl)]-1,2,6,7,8,12b-hexahydro-6-oxopyrido[2,1-a][2]benzazepine (32 mg, 0.09 mmol) and sulfuric acid (1.0 mL, 95–98%) in a pressure vessel. Add carbon monoxide (gas) by sparge to a pressure of 45 psi. After 18 hours, add water (10 mL). Extract the reaction mixture with ethyl acetate. Extract the organic layer with saturated aqueous potassium carbonate solution (5×10 mL). Combine the aqueous layers and carefully acidify with aqueous 12M hydrochloric acid solution. Extract with chloroform (5×15 mL). Combine the organic layers, dry over MgSO$_4$, filter, and evaporate in vacuo to give a residue. Chromatograph the residue on silica gel to give the title compound.

EXAMPLE 3.3

(S)-7-[(1,3-Dihydro-1,3-dioxo-2H-isoindol-2-yl)]-1,2,3,4,6,7,8,12b-octahydro-6-oxopyrido[2,1-a][2]benzazepine-4-carboxylic acid Combine (S)-7-[(1,3-dihydro-1,3-dioxo-2H-isoindol-2-yl)]-1,2,6,7,8,12b-hexahydro-6-oxopyrido[2,1-a][2]benzazepine (800 mg, 2.2 mmol) and sulfuric acid (24 mL) in a pressure vessel. Carefully, add formic acid (4.0 mL, 87 mmol) to minimize mixing and thereby the formation of carbon monoxide. Seal the pressure vessel and add carbon monoxide to 300 psi before stirring. (Caution, upon mixing a sharp rise in pressure will occur.) After 16 hours, vent the vessel and add the reaction mixture to an ice/water mixture (160 mL). Extract repeatedly with ethyl acetate. Combine the organic layers and extract repeatedly with aqueous 10% potassium bicarbonate solution. Combine the potassium bicarbonate solution layers and cool in an ice-bath. Acidify to pH 1 using aqueous 6M hydrochloric acid solution. Extract the acidified aqueous layer repeatedly with ethyl acetate. Combine the organic layers and extract with saturated aqueous sodium chloride solution, dry over MgSO$_4$, filter, and evaporate in vacuo to give the title compound.

EXAMPLE 4

Synthesis of N-[2(S)-(1,3-dihydro-1,3-dioxo-2H-isoindol-2-yl)-1-oxo-3-phenylpropyl]-2-cyano-1,2,3,4-tetrahydro-pyridine

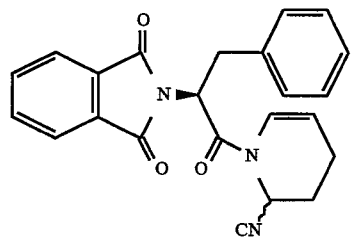

Generate 2-cyano-1,2,3,4-tetrahydro-pyridine in situ, combine 2,6-dicyano-piperidine (1.0 g, 7.4 mmol) tetrahydrofuran (20 mL). Cool to about −23° C. using a dry ice/carbon tetrachloride bath. Slowly, add potassium t-butoxide (0.913 g, 95%, 8.14 mmol). Slow addition of the potassium t-butoxide is required to minimize the formation of by-products. After the addition of potassium t-butoxide is complete, the reaction mixture is stirred for 20–30 minutes to give a solution of 2-cyano-1,2,3,4-tetrahydro-pyridine. Warm the solution to ambient temperature. Add N-phthaloyl-(S)-phenylalanine, acid chloride (2.55 g, 8.14 mmol) and N-methylmorpholine (0.8 mL, 7.4 mmol). After 2 hours, partition the reaction mixture between chloroform and and aqueous 1M sodium bicarbonate solution. Separate the organic layer, dry over MgSO$_4$, filter, and evaporate in vacuo to give a residue. Chromatograph the residue on silica gel eluting with 25% ethyl acetate/hexane to give the title compound.

EXAMPLE 5

Synthesis of 4-cyano-(S)-7-[(1,3-dihydro-1,3-dioxo-2H-isoindol-2-yl)]-1,2,3,4,6,7,8,12b-octahydro-6-oxopyrido[2,1-a][2]benzazepine

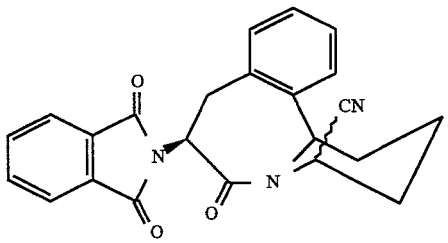

Combine N-[2(S)-(1,3-dihydro-1,3-dioxo-2H-isoindol-2-yl)-1-oxo-3-phenylpropyl]-2-cyano-1,2,3,4-tetrahydropyridine (100 mg, 0.26 mmol), sulfuric acid (3 mL, 99.999%), and trifluoroacetic anhydride (0.03 mL). After 24 hours, the title compound is obtained as a solution.

EXAMPLE 6

(S)-7-[(1,3-Dihydro-1,3-dioxo-2H-isoindol-2-yl)]-1,2,3,4,6,7,8,12b-octahydro-6-oxopyrido[2,1-a][2]benzazepine-(S)-4-carboxylic acid Combine a solution of 4-cyano-(S)-7-[(1,3-dihydro-1,3-dioxo-2H-isoindol-2-yl)]-1,2,3,4,6,7,8,12b-octahydro-6-oxopyrido[2,1-a][2]benzazepine as obtained in Example 5 and water (30 mL). After 3 hours, extract the reaction mixture with chloroform. Separate the organic layer, dry over Na$_2$SO$_4$, filter, and evaporate in vacuo to give a residue (10:1 mixture of S:R isomers at the 4-position carboxylic acid as determined by NMR analysis). Chromatograph the residue on silica gel eluting sequentially with ethyl acetate and then ethyl acetate/acetic acid 99/1 to give the title compound. $[\alpha]^{20}_D = -60.74°$ (c=0.915, MeOH)

PREPARATION 4

Preparation of [4S-[4α, 7α(R*), 12bβ]]-7-[(1-Oxo-2(S)-acetylthio-3-phenylpropyl)amino]-1,2,3,4,6,7,8,12b-octahydro-6-oxo-pyrido[2,1-a][2]benzazepine-4-carboxylic acid Synthesis of [4S-[4α, 7α(R*), 12bβ]]-7-(Amino)-1,2,3,4,6,7,8,12b-octahydro-6-oxopyrido[2,1-a][2]benzazepine-4-carboxylic acid Combine [4S-[4α,7α(R*), 12bβ]]-7-[(1,3-dihydro-1,3-dioxo-2H-isoindol-2-yl)]-1,2,3,4,6,7,8,12b-octahydro-6-oxopyrido[2,1-a][2]benzazepine-4-carboxylic acid (1.63 kg, 4.03 mol), triethylamine (429 g, 4.24 mol), and methanol (5.59 kg). Add hydrazine monohydrate (241 g, 4.82 mol). Heat at reflux. After 3 hours, cool to 60° C. and pour the reaction mixture into a mixture of water (7.326 kg) and aqueous 37% hydrochloric acid solution (821 g). Evaporate in vacuo at 50° C. until the reaction mixture is reduced about 7.8 kg. Dilute the reaction mixture with water (8.078 kg) and adjust the pH to about 2.82 using aqueous 37% hydrochloric acid solution. Heat to 50° C. After 1 hour, filter to remove the solids and rinse with water (pH adjusted to 2.5 with hydrochloric acid, 1.502 kg). Combine the filtrate and the rinse. Adjust the pH to 7.22 using triethylamine. Evaporate in vacuo at 60° C. until the reaction mixture is reduced to about 4.65 kg to obtain a slurry. Dilute the slurry with isopropanol (3.53 kg) and stir for 30 minutes. Cool to 5° C. to obtain a solid. Collect the solid by filtration, rinse with isopropanol, and dry to give the title compound (933 g, 84.4%).

Synthesis of [4S-[4α, 7'(R*), 12bβ]]-7-[(1-Oxo-2(R)-bromo-3-phenylpropyl)amino]-1,2,3,4,6,7,8,12b-octahydro-6-oxo-pyrido[2,1-a][2]benzazepine-4-carboxylic acid Mix 3-phenyl-2(R)-bromopropionic acid (967 g, 4.22 mol), tetrahydrofuran (7.74 kg) and N-hydroxysuccinimide (607 g, 5.27 mol) and cool to 5° C. Add, by slow addition over 2.5 hours, a solution of 1,3-dicyclohexylcarbodiimide (828 g, 4.01 mol) in tetrahydrofuran (1.936 kg), maintaining the temperature between −3° and 3° C. Stir for 19 hours, remove 2,3-dicyclohexylurea by vacuum filtration and wash the filter cake with tetrahydrofuran (1.927 kg). Place the filtrate and wash in a 50 L bottom-drain round-bottom flask, add [4S-[4', 7'(R*), 12bβ]]-7-(amino)-1,2,3,4,6,7,8,12b-octahydro-6-oxo-pyrido[2,1-a][2]benzazepine-4-carboxylic acid (869 g, 3.17 mol) and stir at 22° C. for 5.5 hours. Add triethylamine (77 g, 0.76 mol) and stir for an additional 17 hours at 22° C. Dilute with ethyl acetate (10.427 kg), wash with water (9.94 kg) with 37% hydrochloric acid (214.2 g) and sodium chloride (418 g), then with 12.328 kg water with sodium chloride (418 g). Dry (MgSO$_4$), filter and wash the filter cake with ethyl acetate (2.193 kg). Evaporate the solvent in vacuo, add isopropanol (4.210 kg), stir at 12°–16° C. for 17 hour, chill and isolate the product by vacuum filtration. Wash with isopropanol (621 g) and dry to give the title compound (940 g, 61%).

Synthesis of [4S-[4α, 7β(R*), 12bβ]]-7-[(1-Oxo-2(S)-acetylthio-3-phenylpropyl)amino]-1,2,3,4,6,7,8,12b-octahydro-6-oxo-pyrido[2,1-a][2]benzazepine-4-carboxylic acid Mix [4S-[4β, 7α(R*), 12bβ]]-7-[(1-oxo-2(R)-bromo-3-phenylpropyl)amino]-1,2,3,4,6,7,8,12b-octahydro-6-oxo-pyrido[2,1-a][2]benzazepine-4-carboxylic acid (1.052 kg, 2.17 mol), acetone (13.256 kg) and thiolacetic acid (207.1 g, 2.72 mol). Cool to −2° C. and add, over approximately 10 minutes, a solution of potassium hydroxide (279.5 g) in water (270 g). Stir at −4° C. for 23 hours, add 1.054 kg water containing 37% hydrochloric acid (210 g) and evaporate the solvent in vacuo. Dissolve the solid residue in toluene (11.517 kg) at 43° C., transfer to a 22 L bottom-drain round bottom flask and wash with water (4.067 kg). Wash at 41° C. with 4.099 kg water containing sodium chloride (213 g). Evaporate the solvent in vacuo, dissolve the solid residue in toluene (10.239 kg), filter and cool. After cooling to −2° C., collect the solid by vacuum filtration, wash with toluene (1.103 kg) and dry under vacuum at up to 80° C. to give the title compound (859 g, 82.5%).

Preparation of [4S-[4α, 7α(R*), 12bβ]]-7-[(1-Oxo-2(S)-thio-3-phenylpropyl)amino]-1,2,3,4,6,7,8,12b-octahydro-6-oxo-pyrido[2,1-a][2]benzazepine-4-carboxylic acid Dissolve [4S-[4α, 7'(R*), 12bβ]]-7-[(1-oxo-2(S)-acetylthio-3-phenylpropyl)amino]-1,2,3,4,6,7,8,12b-octahydro-6-oxo-pyrido[2,1-a][2]benzazepine-4-carboxylic acid (57 mg, 0.12 mmol) in deoxygenated methanol (3 mL) containing lithium hydroxide (0.25 mL, 1M in water, 0.25 mmol). Stir for 30 minutes under argon atmosphere at ambient temperature. Reduce in volume to 1.5 mL in vacuo, then add, by dropwise addition, to a rapidly stirring solution of 2M hydrochloric acid (2 mL). Collect the resulting precipitate, wash with water and dry in a vacuum dessicator for 1 hour. Dry at 35° C. overnight to give the title compound as a white electrostatic powder.

What is claimed is:

1. A process for preparing a compound of the formula

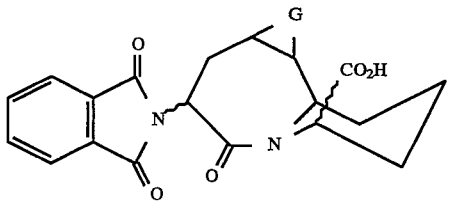

wherein

G completes an aromatic ring selected from the group consisting of

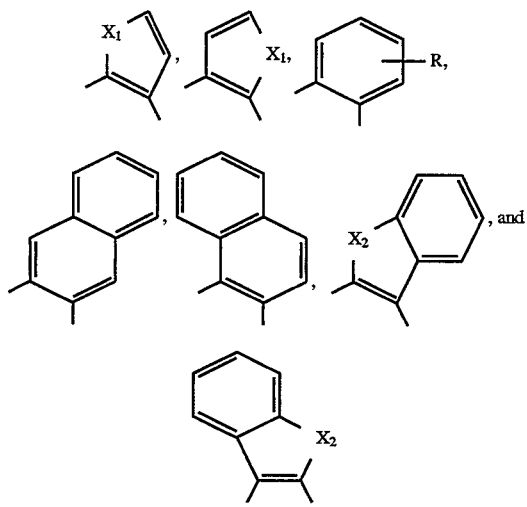

wherein $X_1$ is selected from the group consisting of S and NH;

$X_2$ is selected from the group consisting of S, O, and NH; and

R is selected from the group consisting of hydrogen, hydroxy, phenyl, and $C_1$–$C_4$ alkoxy; comprising:

(a) reacting a phthalimido aryl amino acid amide of the formula

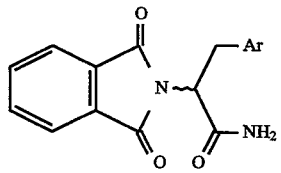

wherein

Ar is a radical selected from the group consisting of

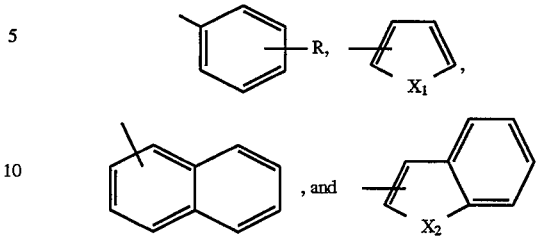

wherein $X_1$ is selected from the group consisting of S and NH;

$X_2$ is selected from the group consisting of S, O, and NH; and

R is selected from the group consisting of hydrogen, hydroxy, phenyl and $C_1$–$C_4$ alkoxy;

with glutaric dialdehyde to give a 1,4-dihydropyridine derivative of the formula

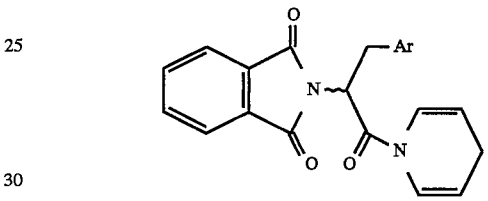

wherein Ar is as defined above;

(b) reacting the 1,4-dihydropyridine derivative with an appropriate cyclizing acid to give a 1,2,6,7,8,12b hexahydro-6-oxopyrido[2,1-a][2]azepine of the formula

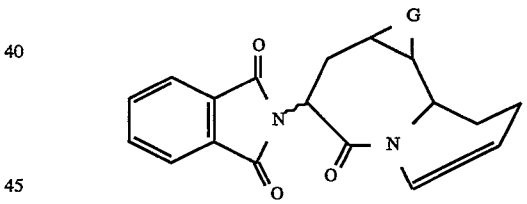

wherein G is as defined above;

(c) reacting the 1,2,6,7,8,12b hexahydro-6-oxopyrido[2,1-a][2]azepine with carbon monoxide in the presence of a suitable acid followed by hydration.

2. A process according to claim 1 wherein the appropriate cyclizing acid is a trifluoromethanesulfonic acid/ trifluoroacetic anhydride mixture.

3. A process according to claim 1 wherein the appropriate cyclizing acid is sulfuric acid/trifluoroacetic anhydride mixture.

* * * * *

UNITED STATES PATENT AND TRADEMARK OFFICE
CERTIFICATE OF CORRECTION

PATENT NO. : 5,641,880

DATED : June 24, 1997

INVENTOR(S) : Gary A. Flynn, et al.

It is certified that error appears in the above-identified patent and that said Letters Patent is hereby corrected as shown below:

At column 4, line 50, the patent reads "-cyano" and should read -- 4-cyano --.
At column 7, line 46, the patent reads "refer" and should read --refers--.
At column 8, line 10, the patent reads "may attached" and should read --may be attached--.
At column 11, lines 7, 9, 29 and 31, the patent reads "7β(R*)" and should read -- 7α(R*) --.
At column 13, line 52, the patent reads "Examples appropriate" and should read --Examples of appropriate--.
At column 18, line 28, the patent reads "-2-Vl)" and should read -- -2-yl) --.
At column 19, line 9, the patent reads "8f12b" and should read -- 8, 12b --.
At column 22, line 6 and 19, the patent reads "7'(R*)" and should read --7α(R*)--.
At column 22, line 33 the patent reads "7β(R*)" and should read -- 7α(R*) --.
At column 22, line 38, the patent reads "[4β" and should read -- [4α --.
At column 22, line 60, the patent reads "7'(R*)" and should read --7α(R*)--

Signed and Sealed this

Twenty-seventh Day of October, 1998

Attest:

BRUCE LEHMAN

Attesting Officer     Commissioner of Patents and Trademarks